US010330721B2

(12) United States Patent
Kume et al.

(10) Patent No.: US 10,330,721 B2
(45) Date of Patent: Jun. 25, 2019

(54) OIL RESISTANCE TEST METHOD AND OIL RESISTANCE TEST APPARATUS

(71) Applicant: OMRON Corporation, Kyoto-shi, Kyoto (JP)

(72) Inventors: Tsutomu Kume, Kusatsu (JP); Tomoyuki Maki, Kusatsu (JP); Kyoji Kitamura, Uji (JP); Masaki Nakamura, Kyoto (JP)

(73) Assignee: OMRON CORPORATION, Kyoto (JP)

( * ) Notice: Subject to any disclaimer, the term of this patent is extended or adjusted under 35 U.S.C. 154(b) by 155 days.

(21) Appl. No.: 15/425,449

(22) Filed: Feb. 6, 2017

(65) Prior Publication Data

US 2017/0285093 A1    Oct. 5, 2017

(30) Foreign Application Priority Data

Mar. 31, 2016 (JP) ................... 2016-071146

(51) Int. Cl.
*G01R 31/12* (2006.01)
*G01R 31/00* (2006.01)
(Continued)

(52) U.S. Cl.
CPC ....... *G01R 31/1263* (2013.01); *G01N 17/002* (2013.01); *G01N 33/442* (2013.01); *G01R 31/003* (2013.01)

(58) Field of Classification Search
CPC ...... G01R 31/00; G01R 31/003; G01R 31/12; G01R 31/1227; G01R 31/1263;
(Continued)

(56) References Cited

U.S. PATENT DOCUMENTS

| 2012/0074968 A1 | 3/2012 | Chu et al. |
| 2012/0103655 A1 | 5/2012 | Imabayashi et al. |

(Continued)

FOREIGN PATENT DOCUMENTS

| CN | 102087188 A | 6/2011 |
| CN | 102379067 A | 3/2012 |

(Continued)

OTHER PUBLICATIONS

Communication dated Jul. 21, 2017 issued by the European Patent Office in counterpart application No. 17155245.8.
(Continued)

*Primary Examiner* — Hoai-An D. Nguyen
(74) *Attorney, Agent, or Firm* — Sughrue Mion, PLLC

(57) ABSTRACT

An oil resistance test method for an electronic device is provided. At least one type of resin material is provided on at least a portion of an outer surface of the electronic device. The oil resistance test method includes: setting a test temperature; and immersing the electronic device in a water-soluble cutting oil in an atmosphere of the set test temperature. This cutting oil contains a mineral oil and a surfactant, and exhibits a milky-white appearance when diluted with water. The oil resistance test method further includes: determining, based on an electrical characteristic of the electronic device, whether or not the electronic device has been degraded by the cutting oil; and estimating, based on a total immersion time of the electronic device in the cutting oil until degradation of the electronic device is detected, a life of oil resistance of the electronic device.

13 Claims, 9 Drawing Sheets

(51) Int. Cl.
*G01N 17/00* (2006.01)
*G01N 33/44* (2006.01)

(58) Field of Classification Search
CPC ...... G01N 17/00; G01N 17/002; G01N 33/00; G01N 33/44; G01N 33/442
USPC .............. 324/500, 537, 541, 544, 551, 557; 361/679.01, 807, 812
See application file for complete search history.

(56) References Cited

U.S. PATENT DOCUMENTS

2016/0108165 A1\* 4/2016 Takahashi ................ C08L 33/20
166/376
2016/0298415 A1\* 10/2016 Takahashi ........... E21B 33/1208

FOREIGN PATENT DOCUMENTS

| | | |
|---|---|---|
| CN | 104031327 A | 9/2014 |
| EP | 2774963 A1 | 9/2014 |
| JP | 1-170929 U | 12/1989 |

OTHER PUBLICATIONS

Office Action dated Mar. 7, 2019 in Chinese Application No. 201710068566.1.

\* cited by examiner

FIG.3

| MATERIAL NAME | ESTER GROUP | GLASS TRANSITION POINT $T_g(°C)$ | SETTABLE TEMPERATURE |
|---|---|---|---|
| PBT (POLYBUTYLENE TEREPHTHALATE) | PRESENT | 40~60 | 55°C |
| EP (EPOXY RESIN) | PRESENT | 52~100 | 55°C |
| PEI (POLYETHER IMIDE) | ABSENT | 200 | 70°C |
| PMMA (POLYMETHYL METHACRYLATE) | PRESENT | 100 | 70°C |
| PFA (TETRAFLUOROETHYLENE-PERFLUOROALKYL VINYL ETHER COPOLYMER) | ABSENT | 75 | 70°C |

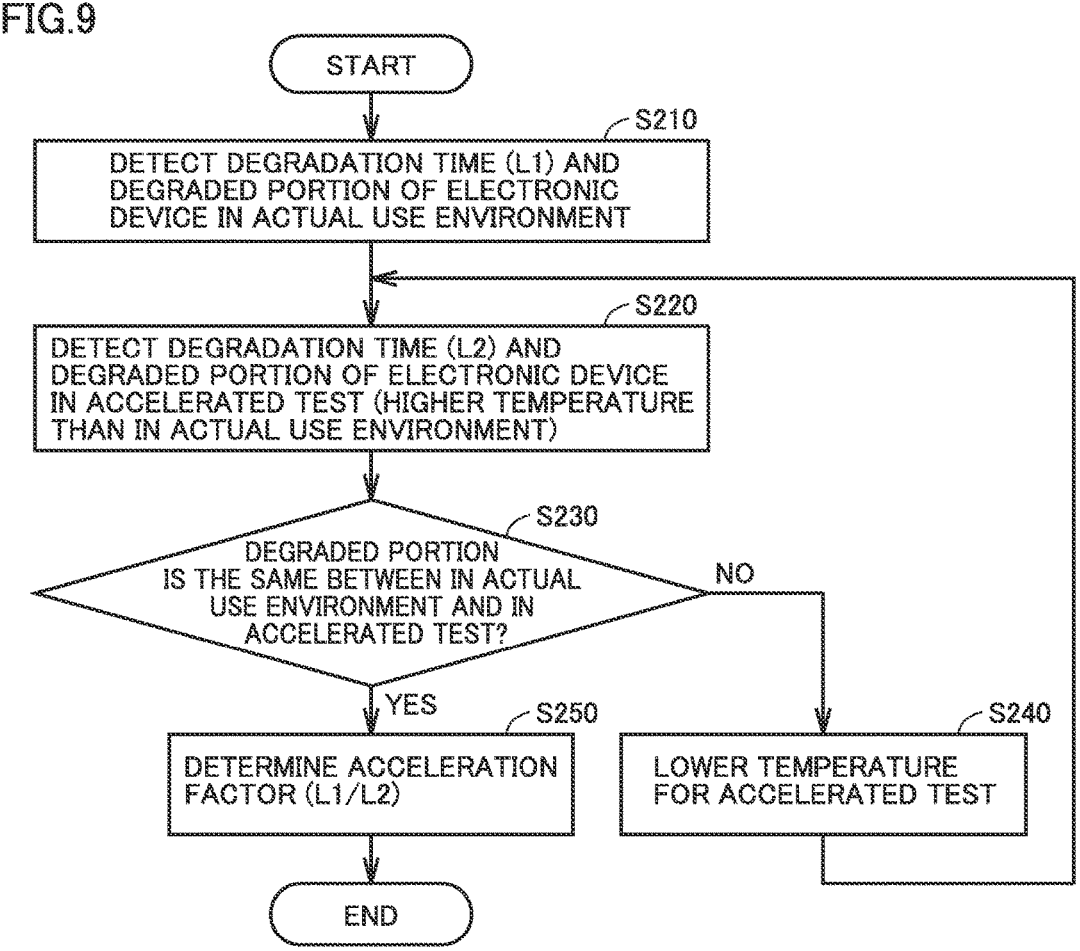

OIL RESISTANCE TEST METHOD AND OIL RESISTANCE TEST APPARATUS

BACKGROUND OF THE INVENTION

Field of the Invention

The present disclosure relates to oil resistance test methods and oil resistance test apparatuses for electronic devices.

Description of the Background Art

A fluororesin material or metal is often used for an exposed portion of an electronic device in order to increase oil resistance and the like. A detection switch disclosed in Japanese Utility Model Laying-Open No. 1-170929 (PTD 1), for example, includes: a tube case made of fluororesin and opened at one end; a cover body made of fluororesin for closing this case opening; and a cable connected to a detection element at the tip and having a sheath made of fluororesin. The cover body is welded to the cable in the vicinity of the detection element, with the cable extending through the cover body. The tube case is provided with the detection element inserted therein, and is sealed with the cover body welded to the opening.

SUMMARY OF THE INVENTION

In developing a variety of electronic devices such as a sensor for use in a machine tool and the like, it is important to evaluate how oil resistant these electronic devices are to a cutting oil in the actual use environment. Although an accelerated evaluation test needs to be conducted in order to efficiently evaluate the oil resistance, specific conditions under which the accelerated evaluation test should be conducted have not been clearly established.

An object of the present disclosure is to provide an oil resistance test method and an oil resistance test apparatus for determining the life of an electronic device with respect to a cutting oil.

The present disclosure provides an oil resistance test method for an electronic device as one embodiment. At least one type of resin material is provided on at least a portion of an outer surface of this electronic device. The oil resistance test method includes: setting a test temperature; and immersing the electronic device in a water-soluble cutting oil in an atmosphere of the set test temperature. The cutting oil contains a mineral oil and a surfactant, and exhibits a milky-white appearance when diluted with water. The oil resistance test method further includes: determining, based on an electrical characteristic of the electronic device, whether or not the electronic device has been degraded by the cutting oil; and estimating, based on a total immersion time of the electronic device in the cutting oil until degradation of the electronic device is detected, a life of oil resistance of the electronic device.

Using the water-soluble cutting oil as described above can facilitate swelling, contraction and decomposition of the resin material, thereby reducing a test time of an accelerated test.

The at least one type of resin material may include one or more types of resin materials each having an ester group. In this case, the test temperature is preferably set based on a resin material having the lowest glass transition temperature among the one or more types of resin materials each having an ester group. When such a resin material having an ester group and a low glass transition temperature is included, a low test temperature needs to be set in order to avoid rapid degradation of the resin material.

Preferably, determining whether or not the electronic device has been degraded includes determining whether or not an insulation resistance value of the electronic device has become equal to or less than a reference value. The degradation of the electronic device can be readily determined by the measurement of the insulation resistance in this manner. It is noted that an electronic device as used herein means, when a cable is directly connected to a body portion (that is, when a cable is directly mounted to a body portion without a connector provided on the body portion interposed therebetween), not only the body portion but the entirety including the cable directly connected to the body portion.

Preferably, determining whether or not the electronic device has been degraded includes determining whether or not the electronic device operates normally in an energized state. The degradation of the electronic device can be readily determined by the determination of whether or not the electronic device operates normally in this manner.

Preferably, the oil resistance test method further includes, when it is detected that the electronic device has been degraded, determining which one of a plurality of divided portions of the electronic device has been degraded by measuring insulation resistance of each portion of the plurality of portions.

Preferably, an estimated value of the life is calculated by multiplying the total immersion time by a predetermined acceleration factor. Here, the acceleration factor is calculated, using first and second electronic devices of an identical design, by a ratio between a time until the first electronic device is degraded in an actual use environment, and a total immersion time of the second electronic device in the cutting oil until the second electronic device is degraded at a part identical to a degraded part of the first electronic device in the atmosphere of the test temperature. In this manner, in order to properly conduct an accelerated test, it is required to confirm that the same phenomenon as that in the actual use environment is reproduced in the accelerated test, and the acceleration factor is determined after this reproducibility has been confirmed.

The present disclosure provides an oil resistance test apparatus for an electronic device as another embodiment. The oil resistance test apparatus includes a constant temperature oven, a container, an insulation resistance meter, and a controller. The container is provided in the constant temperature oven, for containing a water-soluble cutting oil in which the electronic device is to be immersed. The insulation resistance meter is for measuring insulation resistance of the electronic device through the water-soluble cutting oil. The controller controls a temperature of the constant temperature oven to be constant. The controller further determines whether or not the insulation resistance of the electronic device has become equal to or less than a reference value.

According to the configuration of the oil resistance test apparatus described above, the insulation resistance can be measured while the electronic device to be tested is simultaneously immersed in the cutting oil in the constant temperature oven.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 3 is a diagram showing a relationship between resin materials and settable test temperatures in table form.

FIG. 9 is a flowchart showing the procedure of determining an acceleration factor.

DESCRIPTION OF THE PREFERRED EMBODIMENTS

Embodiments will be described below in detail with reference to the drawings. It is noted that the same or corresponding parts are designated by the same reference signs, and description thereof will not be repeated.

[General Configuration of Oil Resistance Test Apparatus]

Figure 1:
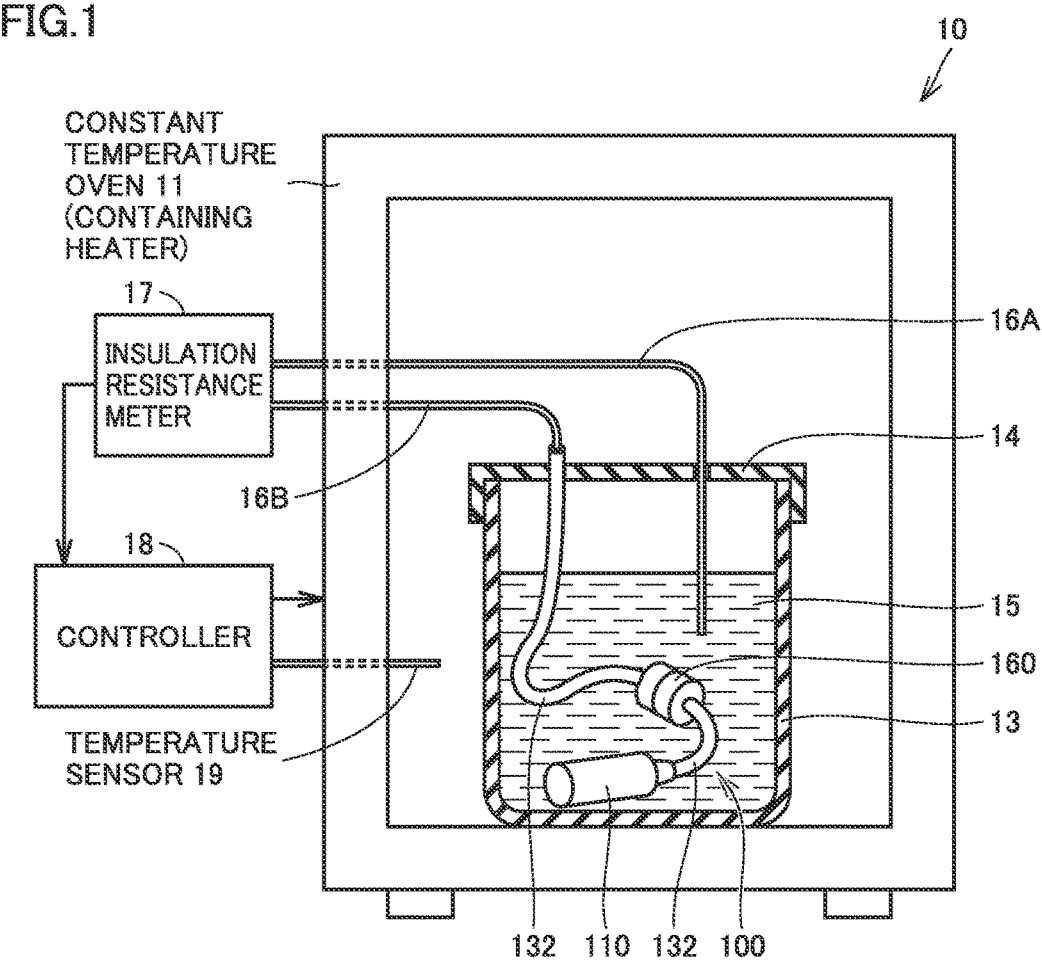
FIG. 1 is a diagram schematically showing an overall configuration of an oil resistance test apparatus.

FIG. 1 is a diagram schematically showing an overall configuration of an oil resistance test apparatus. Referring to FIG. 1, an oil resistance test apparatus 10 includes a constant temperature oven 11, a container 13 with a cover 14 for containing a cutting oil 15, an insulation resistance meter 17, and a controller 18. A front door portion of constant temperature oven 11 is not shown in FIG. 1.

Container 13 with cover 14 is installed in constant temperature oven 11. A cutting oil of Type A1 of the JIS standard K2241 is used as cutting oil 15 (the reason for which will be described later).

An electronic device to be subjected to an accelerated test is immersed in cutting oil 15. Although a proximity sensor 100 is described as an example of the electronic device in FIG. 1, electronic devices in which oil resistance becomes an issue are not limited to proximity sensor 100. Oil resistance to an cutting oil also becomes an issue in a limit switch, a displacement sensor, and a communication device for use in a machine tool, for example.

Figure 2:
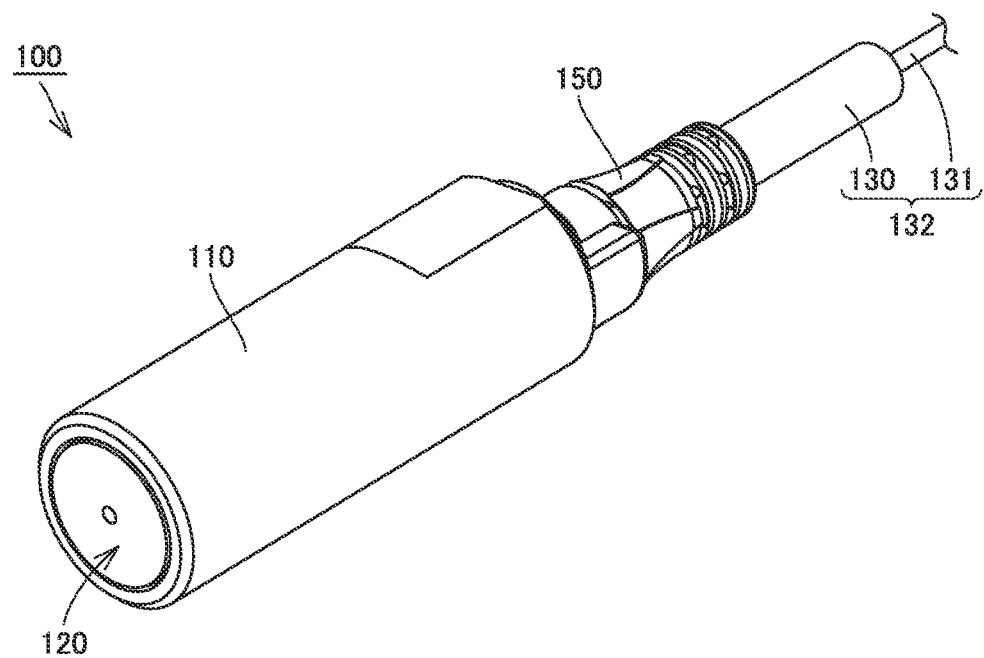
FIG. 2 is a diagram showing an external appearance of a proximity sensor.

FIG. 2 is a diagram showing an external appearance of proximity sensor 100. Referring to FIG. 2, proximity sensor 100 includes an approximately cylindrical enclosure 110 made of metal, a sensing unit assembly 120 attached to a tip end portion of approximately cylindrical enclosure 110, a clamp 150 made of resin and attached to a base end portion of enclosure 110, and a cable 132 fixed to this clamp 150 through a joint interposing member (not shown). An electronic circuit is implemented in enclosure 110. It is noted that cable 132 may be structured such that a plurality of cables 132 are coupled via a connector 160, as shown in FIG. 1 (connector 160 is not needed in the case of a single cable 132).

Sensing unit assembly 120 has a structure in which a core (not shown) and a sensing coil (not shown) are contained in a coil case made of resin (not shown). Cable 132 includes a shielding material (not shown) and a sheath 130 that cover a core 131. Sheath 130 is made of a resin material such as fluororesin. Cable 132 is fixed to clamp 150 through a joint interposing member made of resin. The joint interposing member may be welded to sheath 130 of cable 132 for the purpose of sealing. Core 131 of cable 132 is electrically connected to the electronic circuit (now shown) in enclosure 110.

In the above configuration, the coil case of sensing unit assembly 120, sheath 130 of cable 132, and clamp 150 are made of resin and exposed at the outer surface of proximity sensor 100. Thus, oil resistance of these members becomes an issue.

Unlike the present embodiment, the cable may be fixed to the enclosure of the electronic device through an O ring or rubber bush, instead of clamp 150 and the joint interposing member described above. In this case, the O ring or rubber bush is exposed at the outer surface of the electronic device. Thus, oil resistance of the O ring or rubber bush becomes an issue.

Referring again to FIG. 1, the tip of a measurement cord 16A, which is one of two measurement cords 16A and 16B extending from insulation resistance meter 17, is immersed in a water-soluble cutting oil of Type A1, and the tip of the other measurement cord 16B is connected to the core of cable 132. The insulation resistance of proximity sensor 100 is measured through water-soluble cutting oil 15. It is noted that a portion of the end (end opposite to enclosure 110) of cable 132 that is not covered with sheath 130 must be outside of container 13 with cover 14 containing the water-soluble cutting oil, in order to avoid a short circuit between measurement cords 16A and 16B.

Controller 18 detects an internal temperature of constant temperature oven 11 by a temperature sensor 19, and performs feedback control of an output from a heater (not shown) contained in constant temperature oven 11 such that the interior of constant temperature oven 11 is equal to a user-set test temperature. Controller 18 also determines that a failure has occurred in proximity sensor 100 when a measurement value of the insulation resistance becomes equal to or less than a reference value (for example, 50 MΩ).

Although the insulation resistance of electronic device 100 to be tested is measured while electronic device 100 is simultaneously immersed in cutting oil 15 in constant temperature oven 11 in the above, the insulation resistance may be measured by taking electronic device 100 out of constant temperature oven 11 at regular time intervals. In this case, if there is no abnormality in the insulation resistance of the electronic device, electronic device 100 is put back in constant temperature oven 11 to continue the accelerated test.

[Selection of Cutting Oil]

Although a cutting oil is diluted for use in the actual use environment, a stock solution of a cutting oil is used and an electronic device to be measured is immersed in this stock solution of the cutting oil in an accelerated test. The reason for using a stock solution is because a cutting oil that has intermittently splashed on an electronic device may be potentially dried and condensed on the surface of the electronic device in the actual use environment. Further, for the reasons discussed below, a water-soluble cutting oil termed Type A1 in the JIS standard K2241 is used for the accelerated test. Type A1 refers to those "which are composed of a water-insoluble component such as mineral oil or fatty oil and a surfactant, and which exhibit a milky-white appearance when diluted with water." It is noted that there are additional Type A2 and Type A3 water-soluble cutting oils. Type A2 refers to those "which are composed of a water-soluble component alone such as a surfactant, or composed of a water-soluble component and a water-insoluble component such as mineral oil or fatty oil, and which exhibit a translucent to transparent appearance when diluted with water." Type A3 refers to those "which are composed of a water-soluble component, and which exhibit a transparent appearance when diluted with water."

In general, according to the JIS standard K2241, cutting oils are classified into Type N1 to Type N4 which are four types of water-insoluble cutting oils, and Type A1 to Type A3 which are three types of water-soluble cutting oils. Here, a cutting oil that causes quick progress of degradation of a resin member is selected for use in an accelerated test. Specifically, a cutting oil that facilitates swelling, contraction and decomposition of a resin member is selected. The degree of swelling and contraction is evaluated by a rate of weight change and/or a rate of dimensional change.

First, in terms of decomposition, the water-insoluble cutting oils (Types N1 to N4) are excluded because they do not cause decomposition. Next, among the water-soluble cutting oils (Types A1 to A3), the cutting oil of Type A3 is excluded because it does not contain a mineral oil which is a major contributing factor to swelling and contraction. Further, when the cutting oil of Type A1 and the cutting oil of Type A2 are compared with each other, Type A1 has a higher content of mineral oil and thus causes a higher degree of swelling and contraction. It is thus desirable to use the cutting oil of Type A1 as a cutting oil for an accelerated test. Moreover, a ratio of components in the cutting oil may be adjusted so as to maximize the effect on the resin member.

[Selection of Set Temperature (Test Temperature) of Constant Temperature Oven]

Since an electronic device is usually used in the vicinity of room temperature in the actual use environment, a test temperature for an accelerated test is set to a temperature higher than the use temperature. If a use temperature of an electronic device in the actual use environment is higher than room temperature (for example, in the vicinity of 40° C.), an accelerated test temperature is again set to a temperature higher than the actual use temperature. However, it must be borne in mind that the actual accelerated test temperature has a limiting temperature depending on the resin material exposed at the outer surface of an electronic device to be tested. For example, when a particular resin material is rapidly degraded at a high temperature (for example, when the temperature of a resin material having an ester group exceeds the glass transition point), there will be a significant difference from the actual use environment. When such a material is used, therefore, a low accelerated test temperature needs to be set. Specific examples will be cited and described below.

FIG. 3 is a diagram showing a relationship between resin materials and settable test temperatures in table form. Referring to FIG. 3, when a resin material having an ester group is provided on the outer surface of an electronic device, the test temperature is set to a lower temperature than when the resin material having an ester group is not provided. This is because an ester group undergoes hydrolysis in a water-soluble cutting oil of Type A1. Specifically, in the example of FIG. 3, PBT (polybutylene terephthalate), EP (epoxy resin), and PMMA (polymethyl methacrylate) include an ester group. When these materials are exposed at the outer surface, therefore, the test temperature needs to be set to a lower temperature than when they are not exposed.

Further, when different resin materials are exposed at the outer surface depending on the portion of the electronic device, and a plurality of types of resin materials each having an ester group are exposed at the outer surface of the electronic device, the test temperature is set based on a resin material having the lowest glass transition temperature among those materials. In the example of FIG. 3, when PBT or EP is used, the test temperature is set to 55° C., which is a value substantially equivalent to the glass transition temperatures of these materials. When only PMMA is used as a material having an ester group, the test temperature is set to 70° C. in consideration of the glass transition temperature of PMMA (100° C.).

[Procedure of Accelerated Test]

Figure 4:
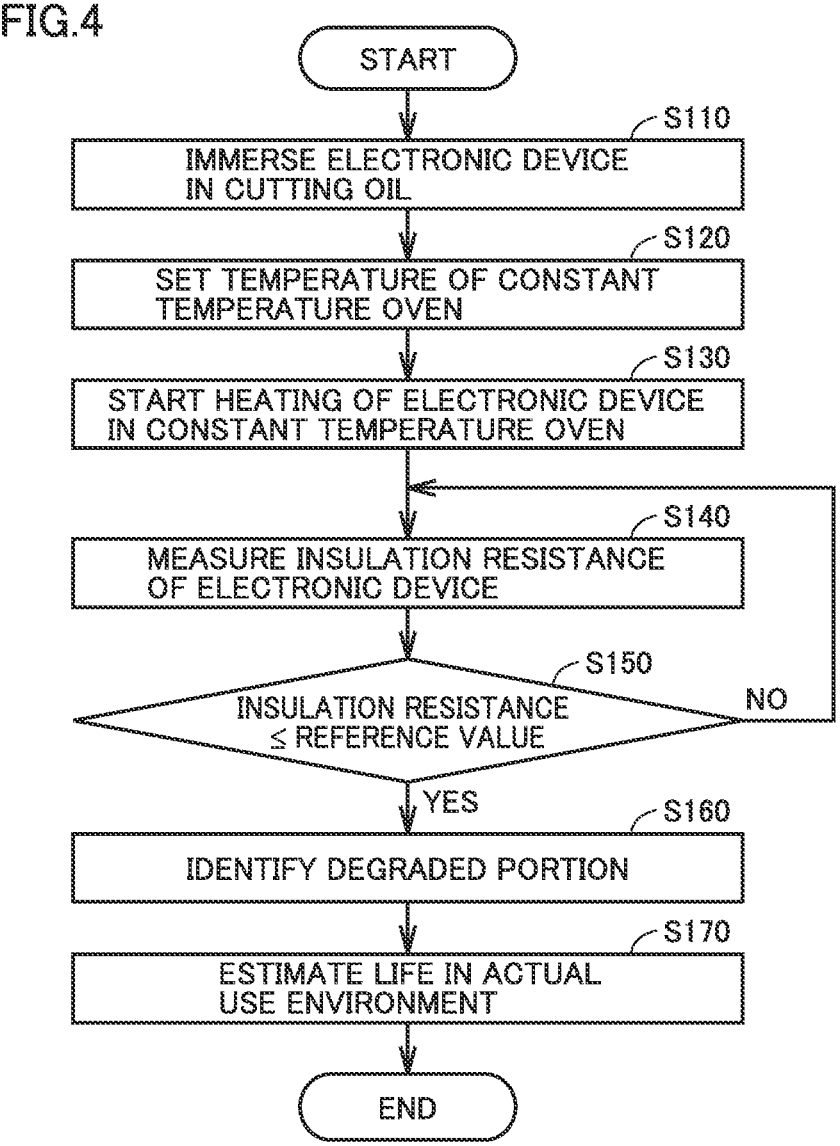
FIG. 4 is a flowchart showing the procedure of an accelerated test.

FIG. 4 is a flowchart showing the procedure of an accelerated test. Referring to FIGS. 1 and 4, the procedure of an accelerated test of oil resistance of an electronic device will be described below.

First, electronic device 100 to be tested is immersed in cutting oil 15 (step S110). Type A1 of the JIS standard K2241 is employed as cutting oil 15. Next, the temperature of constant temperature oven 11 (test temperature) is set depending on the type of a resin material provided on the outer surface of electronic device 100 (step S120). Controller 18 controls an output from the contained heater such that the internal temperature of constant temperature oven 11 becomes equal to the set test temperature, based on a detection value from temperature sensor 19.

Next, heating of electronic device 100 by constant temperature oven 11 is started by placing container 13 with cover 14 containing cutting oil 15 in constant temperature oven 11 together with electronic device 100 (step S130). Further, in the case of the apparatus configuration of FIG. 1, the insulation resistance of electronic device 100 is measured while an accelerated test of oil resistance of electronic device 100 is conducted in an atmosphere of the test temperature (step S140). In contrast to this, the insulation resistance of electronic device 100 may be measured by taking electronic device 100 out of constant temperature oven 11 at regular time intervals.

When the insulation resistance is equal to or less than the reference value (for example, 50 MΩ) as a result of the insulation resistance measurement described above (YES in step S150), it is determined that a failure or degradation has occurred in electronic device 100. Here, instead of measuring the insulation resistance, it may be determined whether or not electronic device 100 operates normally when actually energized.

Here, whether or not electronic device 100 operates normally can be determined based on the following criteria. When the electronic device is a sensor, for example, whether or not the electronic device operates normally is determined based on whether or not a detection value varies. When the electronic device is a switch, whether or not the electronic device operates normally is determined based on whether or not a contact operates properly in response to an input. When the electronic device is a communication device such as an RFID (Radio Frequency Identifier), whether or not the electronic device operates normally is determined based on whether or not the communication device is communicating properly. When the electronic device includes an IO (Input/Output) terminal, whether or not the IO terminal operates normally is determined based on whether or not an internal circuit functions normally. In this manner, the degradation of electronic device 100 can also be determined by measuring the electrical characteristics of electronic device 100 other than the insulation resistance.

Next, when the degradation of electronic device 100 is detected, a degraded portion identified (step S160). Specifically, it is determined which portion has been degraded by measurement of insulation resistances of a plurality of portions.

FIGS. 5 to 8 are diagrams illustrating methods of measuring insulation resistances of enclosure 110, cable 132 between enclosure 110 and connector 160, connector 160, and cable 132 between connector 160 and insulation resistance meter 17, respectively. As shown in FIGS. 5 to 8, electronic device 100 includes enclosure (sensor body) 110 and cable 132 fixed to enclosure 110, where cable 132 has two parts which are connected via connector 160.

Figure 5:
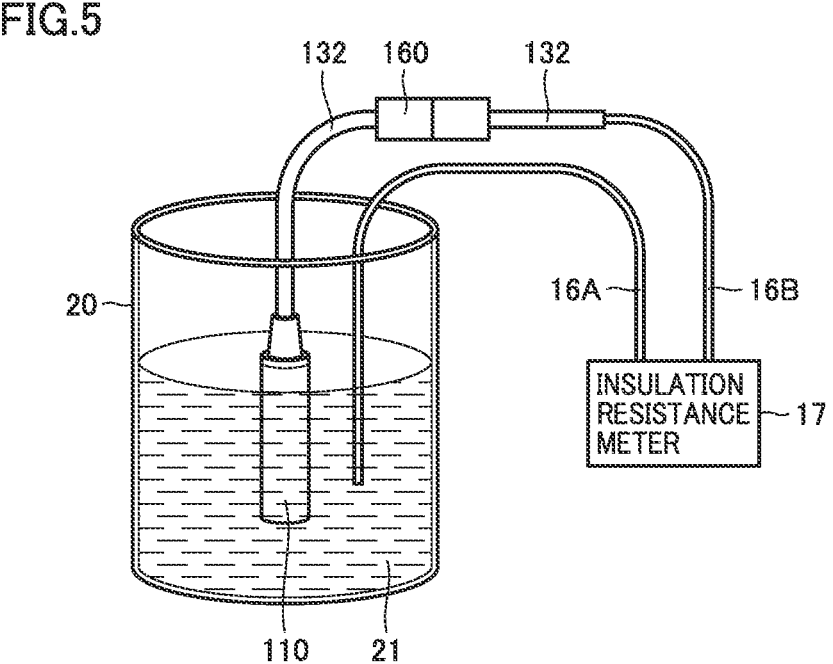
FIG. 5 is a diagram illustrating a method of measuring insulation resistance of an enclosure.

Referring to FIG. 5, when measuring the insulation resistance of only enclosure (sensor body) 110, only enclosure (sensor body) 110 is immersed in water 21 contained in a container 20. In this state, the tip of measurement cord 16A of insulation resistance meter 17 is immersed in the water, and the tip of measurement cord 16B is connected to the core of cable 132. The insulation resistance of only enclosure (sensor body) 110 can thereby be measured through the water. It is noted that a conductive liquid may be used instead of the water in the insulation resistance measurement described above.

When the cable is not directly connected to the enclosure of the electronic device (that is, when the cable is not included in the electronic device), the enclosure of the electronic device is provided with a connector to which the cable can be connected. By attaching a connector pairing with this connector provided on the enclosure to the tip of measurement cord 16B extending from insulation resistance meter 17, the enclosure and measurement cord 16B can be electrically connected to each other to measure the insulation resistance of only the enclosure. Alternatively, the enclosure and measurement cord 16B may be electrically connected to each other through a cable attached at one end to a connector pairing with the connector provided on the enclosure.

Figure 6:
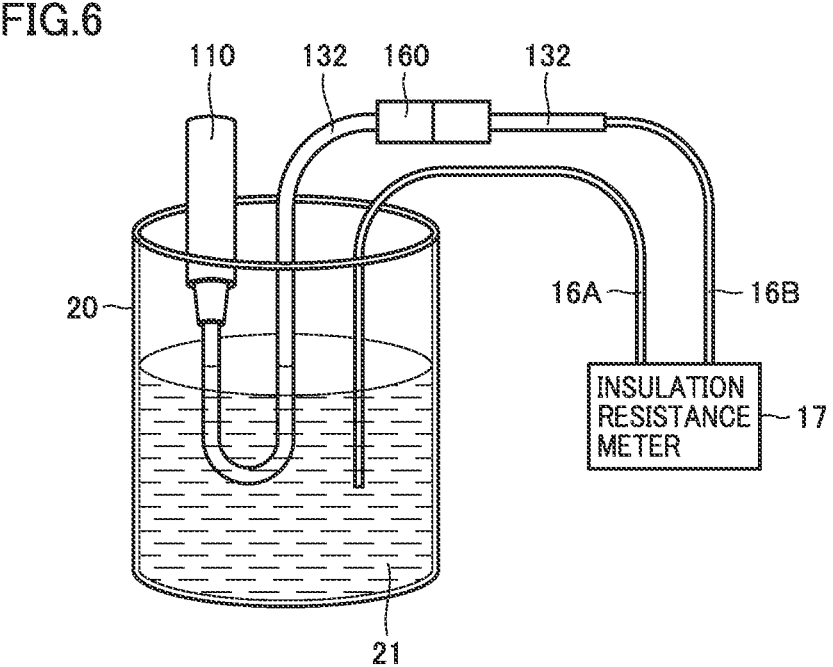
FIG. 6 is a diagram illustrating a method of measuring insulation resistance of a cable between the enclosure and a connector.

Referring to FIG. 6, when measuring the insulation resistance of cable 132 between enclosure 110 and connector 160, the appropriate portion is immersed in the water. In this state, the tip of measurement cord 16A of insulation resistance meter 17 is immersed in the water, and the tip of measurement cord 16B is connected to the core of cable 132. It is noted that when the cable is not directly connected to the enclosure of the electronic device (that is, when the cable is not included in the electronic device), the measurement step of FIG. 6 is skipped.

Figure 7:
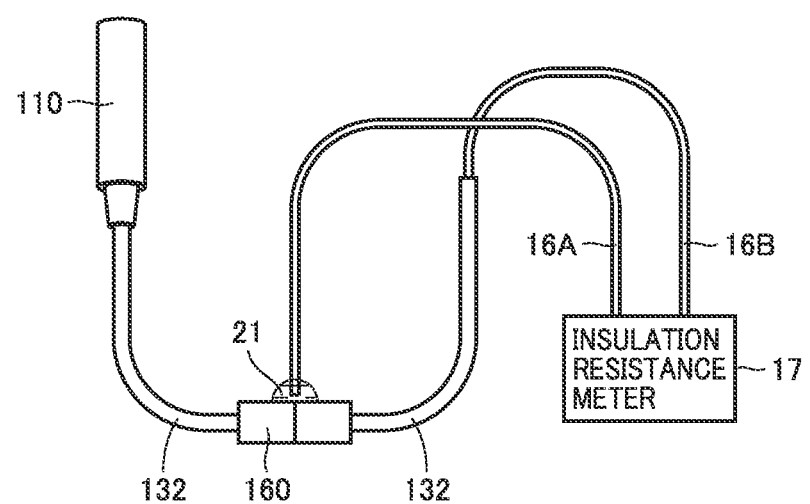
FIG. 7 is a diagram illustrating a method of measuring insulation resistance of the connector.

Referring to FIG. 7, when measuring the insulation resistance of connector 160, the tip of measurement cord 16A of insulation resistance meter 17 is brought into contact with connector 160 while being immersed in the water. The tip of measurement cord 16B is connected to the core of cable 132. It is noted that when the electronic device is not provided with connector 160, the measurement step of FIG. 7 is skipped.

Figure 8:
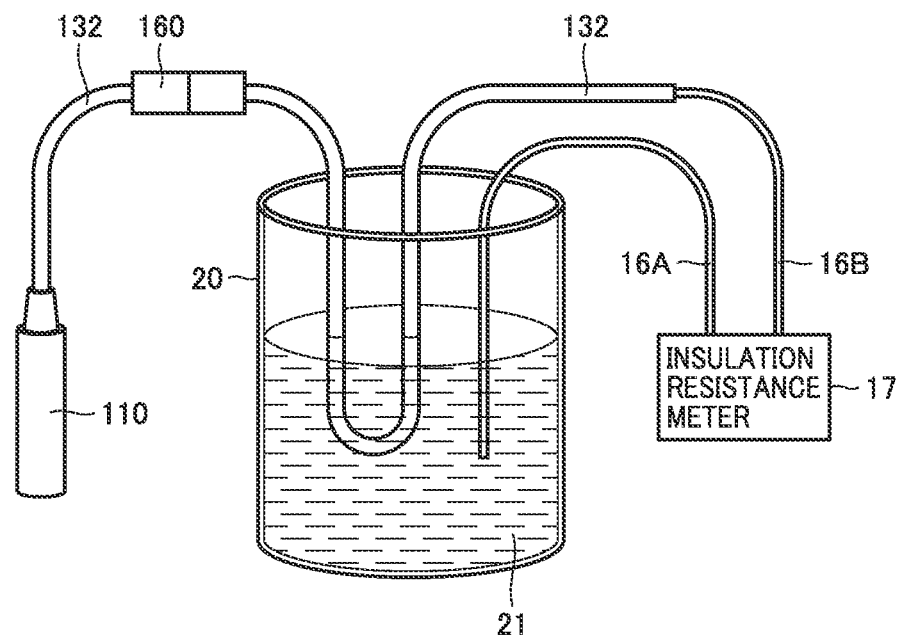
FIG. 8 is a diagram illustrating a method of measuring insulation resistance of the cable between the connector and an insulation resistance meter.

Referring to FIG. 8, when measuring the insulation resistance of cable 132 between connector 160 and insulation resistance meter 17, the appropriate portion is immersed in the water. In this state, the tip of measurement cord 16A of insulation resistance meter 17 is immersed in the water, and the tip of measurement cord 16B is connected to the core of cable 132. It is noted that when the cable is not directly connected to the enclosure of the electronic device (that is, when the cable is not included in the electronic device), the measurement step of FIG. 8 is skipped.

Referring again to FIG. 4, when the degradation of electronic device 100 is detected, the life of the oil resistance of electronic device 100 in the actual use environment is estimated based on a total value of immersion time of electronic device 100 in cutting oil 15 until that point in time (step S170). Specifically, an estimated value of the life of electronic device 100 can be calculated by multiplying the total value of immersion time by a predetermined acceleration factor. The procedure of determining the acceleration factor is described next.

[Procedure of Determining Acceleration Factor]

FIG. 9 is a flowchart showing the procedure of determining the acceleration factor. A plurality of electronic devices (first to third electronic devices hereinafter) of the same design are used in determining the acceleration factor.

First, in the actual use environment, a degradation time (for example, an amount of time until the insulation resistance becomes equal to or less than the reference value) and a degraded portion of the first electronic device are detected (step S210). The methods described with reference to FIGS. 5 to 8 are used to detect the degraded portion.

Next, a degradation time and a degraded portion of the second electronic device are detected by an accelerated test (atmosphere of higher temperature than in the actual use environment, immersion in a cutting oil of Type A1) (step S220). The same method as that in step S210 is used to detect the degradation time and degraded portion.

Next, it is determined whether or not the degraded portion is the same between in the actual use environment and in the accelerated test (step S230). When the degraded portion differs between them (NO in step S230), the test temperature for the accelerated test is changed to a lower temperature (step S240), and the accelerated test (step S220 described above) is conducted again using the third electronic device.

When the degraded portion is the same between in the actual use environment and in the accelerated test, on the other hand, an acceleration factor (L1/L2) is determined from an elapsed time (L1) before the degradation of electronic device 100 in the actual use environment and a total immersion time (L2) in the cutting oil in the accelerated test (step S250). In this manner, in order to properly conduct the accelerated test, it is required to confirm that the same phenomenon as that in the actual use environment is reproduced in the accelerated test, and the acceleration factor (L1/L2) is determined after this reproducibility has been confirmed.

[Advantageous Effects]

According to the above embodiment, the cutting oil of Type A1 of the JIS standard K2241 is used in the accelerated test, thus allowing the accelerated test to be conducted efficiently. Further, the test temperature for the accelerated test is set depending on the resin material used for the electronic device to be tested, so that the same phenomenon as that in the actual use environment can be reproduced in the accelerated test, thus allowing the acceleration factor to be set appropriately.

Although the embodiments the present invention have been described, it should be understood that the embodiments disclosed herein are illustrative and non-restrictive in every respect. The scope of the present invention is defined by the terms of the claims, and is intended to include any modifications within the scope and meaning equivalent to the terms of the claims.

What is claimed is:

1. An oil resistance test method for an electronic device, with at least one type of resin material provided on at least a portion of an outer surface of the electronic device, the oil resistance test method comprising:

setting a test temperature;

immersing the electronic device in a water-soluble cutting oil in an atmosphere of the test temperature, the cutting oil containing a mineral oil and a surfactant and exhibiting a milky-white appearance when diluted with water;

determining, based on an electrical characteristic of the electronic device, whether or not the electronic device has been degraded by the cutting oil; and estimating, based on a total immersion time of the electronic device in the cutting oil until degradation of the electronic device is detected, a life of the electronic device with respect to oil resistance, wherein an estimated value of the life is calculated by multiplying the total immersion time by a predetermined acceleration factor, and wherein the acceleration factor is calculated, using first and second electronic devices of an identical design, by a ratio between a time until the first electronic device is degraded in an actual use environment, and a total immersion time of the second electronic device in the cutting oil until the second electronic device is degraded at a part identical to a degraded part of the first electronic device in the atmosphere of the test temperature.

2. The oil resistance test method according to claim 1, wherein the at least one type of resin material includes one or more types of resin materials each having an ester group, and the test temperature is set based on a resin material having the lowest glass transition temperature among the one or more types of resin materials each having an ester group.

3. The oil resistance test method according to claim 1, wherein determining whether or not the electronic device has been degraded includes determining whether or not an insulation resistance value of the electronic device has become equal to or less than a reference value.

4. The oil resistance test method according to claim 2, wherein determining whether or not the electronic device has been degraded includes determining whether or not an insulation resistance value of the electronic device has become equal to or less than a reference value.

5. The oil resistance test method according to claim 1, wherein determining whether or not the electronic device has been degraded includes determining whether or not the electronic device operates normally in an energized state.

6. The oil resistance test method according to claim 2, wherein determining whether or not the electronic device has been degraded includes determining whether or not the electronic device operates normally in an energized state.

7. The oil resistance test method according to claim 1, further comprising, when it is detected that the electronic device has been degraded, determining which one of a plurality of divided portions of the electronic device has been degraded by measuring insulation resistance of each portion of the plurality of portions.

8. The oil resistance test method according to claim 2, further comprising, when it is detected that the electronic device has been degraded, determining which one of a plurality of divided portions of the electronic device has been degraded by measuring insulation resistance of each portion of the plurality of portions.

9. The oil resistance test method according to claim 3, further comprising, when it is detected that the electronic device has been degraded, determining which one of a plurality of divided portions of the electronic device has been degraded by measuring insulation resistance of each portion of the plurality of portions.

10. The oil resistance test method according to claim 4, further comprising, when it is detected that the electronic device has been degraded, determining which one of a plurality of divided portions of the electronic device has been degraded by measuring insulation resistance of each portion of the plurality of portions.

11. An oil resistance test apparatus for an electronic device, comprising:

a constant temperature oven;

a container provided in the constant temperature oven, for containing a water-soluble cutting oil in which the electronic device is to be immersed;

an insulation resistance meter for measuring insulation resistance of the electronic device through the water-soluble cutting oil; and a controller for controlling a temperature of the constant temperature oven to be constant, wherein:

the controller is configured to determine whether or not the insulation resistance of the electronic device has fallen below a reference value;

the controller is configured to estimate a life of the electronic device with respect to oil resistance, based on a total immersion time of the electronic device in the water-soluble cutting oil until the insulation resistance of the electronic device becomes equal to or less than the reference value;

the controller is configured to calculate an estimated value of the life by multiplying the total immersion time by a predetermined acceleration factor;

the acceleration factor is equal to a value of a ratio between a time until it is determined that a first electronic device has been degraded in an actual use environment based on insulation resistance of the first electronic device becoming equal to or less than the reference value, and a total immersion time of a second electronic device in the cutting oil until it is determined that the second electronic device has been degraded at a portion identical to a degraded portion of the first electronic device in an atmosphere of the test temperature; and the first and second electronic devices are electronic devices of an identical design.

12. The oil resistance test apparatus for an electronic device according to claim 11, wherein at least one type of resin material is provided on at least a portion of an outer surface of the electronic device, and the water-soluble cutting oil contains a mineral oil and a surfactant and exhibits a milky-white appearance when diluted with water.

13. The oil resistance test apparatus for an electronic device according to claim 12, wherein the at least one type of resin material includes one or more types of resin materials each having an ester group, and the controller is configured, during a test of oil resistance of the electronic device, to control the temperature of the constant temperature oven to be equal to a test temperature determined based on a resin material having the lowest glass transition temperature among the one or more types of resin materials each having an ester group.

* * * * *